US007396851B2

(12) United States Patent
Baraldi et al.

(10) Patent No.: US 7,396,851 B2
(45) Date of Patent: Jul. 8, 2008

(54) HETEROCYCLIC AND BENZOHETEROCYCLIC POLYAMIDES STRUCTURALLY RELATED TO THE NATURAL ANTIBIOTIC DISTAMYCIN A FOR THE TREATMENT OF β-THALASSAEMIA

(75) Inventors: Pier Giovanni Baraldi, Ferrara (IT); Nicoletta Bianchi, Mezzogoro (IT); Giordana Feriotto, Occhiobello (IT); Roberto Gambari, Bologna (IT); Carlo Mischiati, Rovigo (IT); Romeo Romagnoli, Ferrara (IT)

(73) Assignees: Universita' Degli Studi Di Ferrara, Ferrara (IT); Associazione Veneta per La Lotta Alla Talassemia, Rovigo (IT); Associazione per La Lotta Alla Talassemia Di Ferrara, Ferrara (IT)

( * ) Notice: Subject to any disclaimer, the term of this patent is extended or adjusted under 35 U.S.C. 154(b) by 262 days.

(21) Appl. No.: 10/481,882

(22) PCT Filed: Jul. 1, 2002

(86) PCT No.: PCT/IB02/02628

§ 371 (c)(1),
(2), (4) Date: Aug. 13, 2004

(87) PCT Pub. No.: WO03/004019

PCT Pub. Date: Jan. 16, 2003

(65) Prior Publication Data

US 2004/0259799 A1 Dec. 23, 2004

(30) Foreign Application Priority Data

Jul. 2, 2001 (IT) .............................. TO01A0633

(51) Int. Cl.
*A61K 31/40* (2006.01)
*C07D 207/00* (2006.01)
*C07D 405/00* (2006.01)

(52) U.S. Cl. ...................... 514/408; 514/422; 514/423; 548/400; 548/517; 548/518; 548/530; 548/537

(58) Field of Classification Search ................ 548/400, 548/517, 518, 530, 537; 514/408, 423, 422
See application file for complete search history.

(56) References Cited

U.S. PATENT DOCUMENTS

| 3,432,522 | A | * | 3/1969 | Preau ........................ 548/518 |
| 4,738,980 | A | * | 4/1988 | Arcamone et al. .......... 514/422 |
| 4,766,142 | A | * | 8/1988 | Arcamone et al. .......... 514/422 |
| 4,912,199 | A | * | 3/1990 | Lown et al. ................ 530/331 |
| 5,175,182 | A | * | 12/1992 | Mongelli et al. ........... 514/428 |
| 5,272,056 | A | * | 12/1993 | Burrows et al. ............... 435/6 |
| 5,446,137 | A | * | 8/1995 | Maag et al. ................ 536/23.1 |
| 6,906,103 | B2 | * | 6/2005 | Zhang et al. ............... 514/579 |
| 7,064,218 | B2 | * | 6/2006 | Dyatkina et al. ............ 548/400 |

FOREIGN PATENT DOCUMENTS

| WO | 94/25436 | 11/1994 |
| WO | 96/05196 | 2/1996 |
| WO | 98/21202 | 5/1998 |
| WO | WO 98 21202 A | 5/1998 |

OTHER PUBLICATIONS

N. Bianchi et al.; "Accumulation of gamma-globin mRNA and induction of erythroid differentiation after treatment of human leukaemic K562 cells with tallimustine"; *British Journal of Haematology*; vol. 113; No. 4; Jun. 2001; pp. 951-961.
N. Bianchi et al.; "The DNA-binding drugs mithramycin and chromomycin are powerful inducers of erythroid differentiation of human K562 cells"; *British Journal of Haematology*; vol. 104; No. 2; Feb. 1999; pp. 258-265.
R. D'Alessio et al.; "Structure-Activity Relationship of Novel Distamycin A Derivatives: Synthesis and Antitumor Activity"; *Bioorganic & Medicinal Chemistry Letters*; vol. 4; No. 12; 1994; pp. 1467-1472.
P. G. Baraldi et al.' :DNA sequence—Recognizing properties of minor groove alkylating agents; *Arzneimittel-Forschung*; vol. 50; No. 3; Mar. 2000; pp. 309-315.
J. DeSimone, et al.; "5-Azacytidine stimulates fetal hemoglobin synthesis in anemic baboons;" *Proc. Natl. Acad. Sci. USA*; vol. 79, pp. 4428-4431; Jul. 1982; Medical Sciences.
C. H. Lowrey, et al.; "Treatment with Azacitidine of Patients with End-Stage β-Thalassemia;" *The New England Journal of Medicine*; vol. 329, pp. 845-848; Sep. 16, 1993; No. 12.
S. P. Perrine, et al.; "A Short-Term Trial of Butyrate to Stimulate Fetal-Globin-Gene Expression in the β-Globin Disorders;" *The New England Journal of Medicine*; vol. 328; pp. 81-86; Jan. 14, 1993; No. 2.
A. Al-Khatti, et al.; "Cooperative Enhancement of F-Cell Formation in Baboons Treated With Erythropoietin and Hydroxyurea;" *Blood*; vol. 72; pp. 817-819; No. 2 (August); 1988.
G. P. Rodgers, et al.; "Augmentation by Erythropoietin of the Fetal-Hemoglobin Response to Hydroxyurea in Sickle Cell Disease;" *The New England Journal of Medicine*; vol. 328; pp. 73-80; Jan. 14, 1993; No. 2.

(Continued)

*Primary Examiner*—Joseph McKane
*Assistant Examiner*—Susannah Chung
(74) *Attorney, Agent, or Firm*—Kratz, Quintos & Hanson, LLP

(57) ABSTRACT

The invention relates to the use of structural analogues of distamycin having the general formula (I), (II), (III), (IV) or (V) or their pharmaceutically acceptable salts, for the preparation of a medicament for the therapeutic treatment of β-thalassaemia.

14 Claims, No Drawings

OTHER PUBLICATIONS

G. P. Rodgers; "Novel Treatment Options in the Severe β-Globin Disorders;" *British Journal of Haematology*; vol. 91; pp. 263-268; 1995.

S. Torkelson, et al.; "Erythroid Progenitor Proliferation is Stimulated by Phenoxyacetic and Phenylalkyl Acids;" *Blood Cells, Molecules, and Diseases*; vol. 22; pp. 150-158; Jul. 31, 1996.

J. Rochette, et al.; "Fetal Hemoglobin Levels in Adults;" *Blood Reviews*; vol. 8; pp. 213-224; 1994.

N. Bianchi, et al.; "Induction of Erythroid Differentiation of Human K562 Cells by Cisplatin Analogs;" *Biochemical Pharmacology*; vol. 60; pp. 31-40; 2000.

N. Bianchi, et al.; "The DNA-binding drugs mithramycin and chromomycin are powerful inducers of erythroid differentiation of human K562 cells;" *British Journal of Haematology*; vol. 104; pp. 258-265; 1999.

S. Castaigne, et al.; "All-Trans Retinoic Acid as a Differentiation Therapy for Acute Promyelocytic Leukemia. I. Clinical Results;" *Blood*; vol. 76; No. 9; pp. 1704-1709; Nov. 1, 1990.

G. J. Dover, et al.; "Increased Fetal Hemoglobin in Patients Receiving Sodium 4-Phenylbutyrate;" *The New England Journal of Medicine*; vol. 327; No. 8; pp. 569-570; Aug. 20, 1992.

T. Ikuta, et al.; "Cellular and Molecular Effects of a Pulse Butyrate Regimen and New Inducers of Globin Gene Expression and Hematopoiesis;" *Annals New York Academy of Sciences*; vol. 850; pp. 87-99; 1998.

R. D'Alessio, et al.; "Structure-Activity Relationship of Novel Distamycin a Derivatives : Synthesis and Antitumor Activity;" *Bioorganic & Medicinal Letters*; vol. 4; No. 12; pp. 1467-1472; 1994.

P. G. Baraldi, et al.; "DNA Sequence-recognizing Properties of Minor Groove Alkylating Agents;" *Arzneimittel-Forschung/Drug Research*; vol. 50 (I); pp. 309-315; 2000.

W. Wang, et al.; "Anti-HIV-I Activity of Linked Lexitropsins;" *J. Med. Chem.*; vol. 35; pp. 2890-2897; 1992.

F. Osti, et al.; "Human Leukemia K562 Cells: Induction to Erythroid Differentiation by Guanine, Guanosine and Guanine Nucleotides;" *Haematologica*; vol. 82; pp. 395-401; 1997.

C. B. Lozzio, et al.; "Human Chronic Myelogenous Leukemia Cell-Line With Positive Philadelphia Chromosome;" *Blood*; vol. 45; No. 3; pp. 321-334; Mar. 1975.

R. Gambari, et al.; "Efficient cell proliferation and predominant accumulation of ε-globin mRNA in human leukemic K562 cells which produce mostly Hb Gower 1;" *Experientia*, vol. 41; pp. 673-675; 1985.

R. Gambari, et al.; "Human leukemia K-562 cells: induction of erythroid differentiation by 5-azacytidine;" *Cell Differentiation*; vol. 14; pp. 87-97; 1984.

T. R. Rutherford, et al.; "K562 human leukaemic cells synthesise embryonic haemoglobin in response to haemin;" *Nature*; vol. 280; pp. 164-165; Jul. 12, 1979.

J. Sambrook, et al., "Electrophoresis of RNA through Gels Containing Formaldehyde;" *Extraction, Purification, and Analysis of Messenger RNA from Eukaryotic Cells*; In: Molecular Cloning $2^{nd}$ ed.; pp. 7.43-7.45; 1981.

E. Fibach; "Techniques for Studying Stimulation of Fetal Hemoglobin Production in Human Erythroid Cultures;" *Hemoglobin*, vol. 22 (5&6); pp. 445-458; 1998.

E. Fibach, et al.; "Hydroxyurea Increases Fetal Hemoglobin in Cultured Erythroid Cells Derived From Normal Individuals and Patients With Sickle Cell Anemia or β-Thalassemia;" *Blood*; vol. 81; No. 6; pp. 1630-1635; Mar. 15, 1993.

C. A. Heid, et al.; "Real Time Quantitative PCR;" *Genome Research*; vol. 6; pp. 986-994, 1996.

U. E. M. Gibson, et al.; "A Novel Method for Real Time Quantitative RT-PCR;" *Genome Research*; vol. 6, pp. 995-1001; 1996.

G. P. Rogers, et al; "Novel Treatment Options in the Severe β-Globin Disorders;" *British Journal of Haematology*; vol. 91; pp. 263-268 (1995).

\* cited by examiner

HETEROCYCLIC AND BENZOHETEROCYCLIC POLYAMIDES STRUCTURALLY RELATED TO THE NATURAL ANTIBIOTIC DISTAMYCIN A FOR THE TREATMENT OF β-THALASSAEMIA

The present invention relates to the use of structural analogues of distamycin capable of inducing erythroid cell differentiation for the preparation of a medicament for the therapeutic treatment of β-thalassaemia.

The existence of substances capable of inducing the biosynthesis of foetal haemoglobin (HbF) in adults has been known for some time (1-7). Those substances are capable of activating the transcription of genes for embryonal and foetal globins and thus of inducing erythroid cell differentiation.

Recently, numerous DNA-binding molecules have been described that have the capacity to bring about an increase in the transcription of globin genes (8). Among these there may be mentioned cisplatin and analogues of cisplatin (9), mithramycin (10) and chromomycin (10). Those substances are referred to herein by the expression "modifiers of the transcription process".

In human beings, activation of the transcription of genes for γ-globins in adults leads to the production of foetal haemoglobin mimicking the phenotype HPFH (High Persistence of Foetal Haemoglobin) which confers a favourable clinical picture on patients suffering from β-thalassaemia, also in homozygotic form (8). A therapy using those molecules in the treatment of patients suffering from β-thalassaemia could therefore make those persons less dependent on transfusion therapy (11-13).

The present invention is therefore based on the need to devise, synthesise and produce novel modifiers of the transcription process that can be used in the treatment of β-thalassaemia and that are capable of bringing about a high level of expression of γ-globin genes.

We have surprisingly found that numerous structural analogues of distamycin, an antibiotic which is described in the prior art and the structural formula of which is illustrated hereinafter, satisfy those requirements.

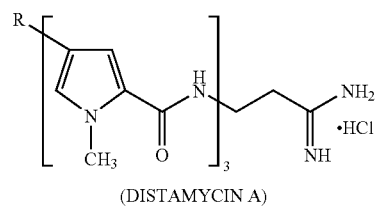

(DISTAMYCIN A)

R = NHCHO

In particular, it has been found that the structural analogues of distamycin, illustrated hereinafter and having the general formulae (I), (II) and (III), (IV) and (V), and their pharmaceutically acceptable salts are capable of inducing erythroid differentiation and the transcription of the gene for human γ-globin.

Analogues of tallimustine containing from 2 to 4 pyrrole rings and having various alkylating units, of the general formula (I):

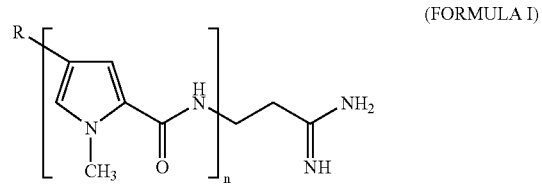

(FORMULA I)

in which:
n is an integer selected from 2, 3 and 4;
R is 4-[(ZCH$_2$CH$_2$)$_2$N]C$_6$H$_4$CONH; and
Z is selected from the group consisting of F, Cl, Br and I.

Analogues of tallimustine in which one or more pyrrole rings have been replaced by an equal number of pyrazole and/or imidazole rings, of the general formula (II):

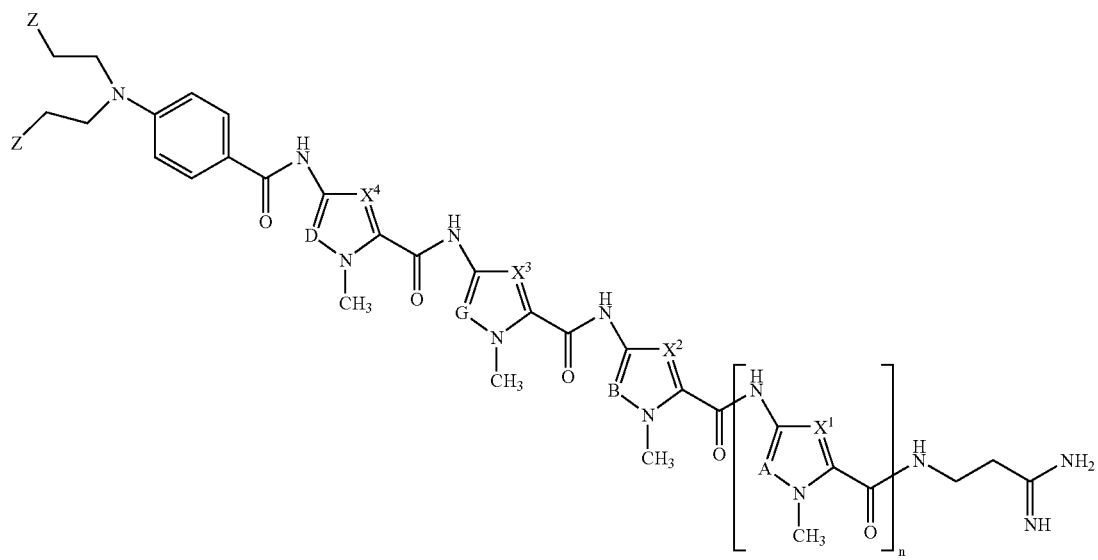

(FORMULA II)

in which:
   n is an integer selected from 0 (zero), 1 and 2;
   Z is selected from the group consisting of F, Cl, Br and I;
   A, B, C and D are selected independently of one another from CH or N;
   $X^1$, $X^2$, $X^3$ and $X^4$ are selected independently of one another from CH or N,
   provided that, when $X^1$ is N, A is CH; when $X^2$ is N, B is CH;
   when $X^3$ is N, C is CH and when $X^4$ is N, D is CH.

Distamycin A derivatives in which the formyl group has been replaced by a benzoheterocycle linked to an alkylating unit, of the general formula (III):

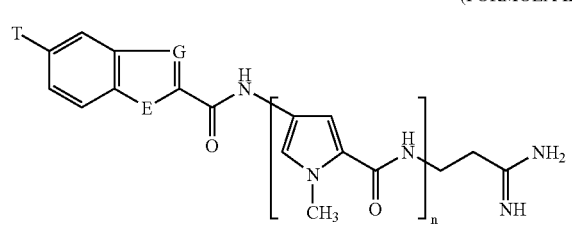

(FORMULA III)

in which:
   n is an integer selected from 2, 3 and 4;
   T is selected from the group consisting of 4-[(ZCH$_2$CH$_2$)$_2$N]C$_6$H$_4$CONH, (ZCH$_2$CH$_2$)$_2$N, and CH$_2$=CZCONH;
   Z is selected from the group consisting of F, Cl, Br and I;
   E is selected from the group consisting of O (oxygen), S and NR$_1$;
   R$_1$ is H or CH$_3$; and
   G is CH or N.

Benzoheterocyclic derivatives of distamycin A in which the pyrrole rings have been replaced by aromatic benzoheterocyclic rings and in which the formyl group has been replaced by an alkylating unit, of the general formula (IV):

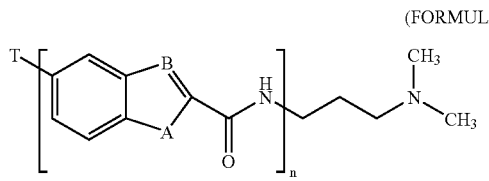

(FORMULA IV)

in which:
   n is an integer selected from 1, 2, 3 and 4;
   T is selected from the group consisting of 4-[(ZCH$_2$CH$_2$)$_2$N]C$_6$H$_4$CONH, (ZCH$_2$CH$_2$)$_2$N, and CH$_2$=CZCONH;
   Z is selected from the group consisting of F, Cl, Br and I;
   A is selected from the group consisting of O (oxygen), S and NR$_1$; R$_1$ is linear or branched alkyl having from 1 to 4 carbon atoms;
   B is CH or N.

Distamycin A analogues modified in the amidine portion and characterized by a double epoxy or oxirane alkylating functionality, of the general formula (V):

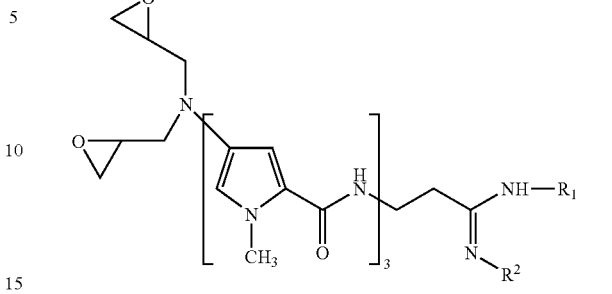

(FORMULA V)

in which:
   R$_1$ and R$_2$ are selected independently of one another from the group consisting of hydrogen, linear or branched alkyl having from 1 to 4 carbon atoms, nitrile (CN) and hydroxyl (OH), or R$_1$ and R$_2$ form, in combination with one another, a linear alkyl chain —(CH$_2$)$_m$— in which m is 2 or 3.

The compounds described above are known per se; their chemical synthesis has been described by various research groups (see, for example, the bibliographical references no. 14 for the compounds of the general formula I, no. 15 for the compounds of the general formula II and no. 16 for the compounds of the general formulae III, IV and V).

However, those compounds were proposed as anti-tumour, anti-viral (16-18) and anti-malarial (19) agents but not as inducers of erythroid cell differentiation.

A first aspect of the present invention is therefore the use of the previously illustrated structural analogues of distamycin having the general formulae (I), (II) and (III), (IV) and (V) and their pharmaceutically acceptable salts, as inducers of erythroid cell differentiation for the preparation of a medicament for the therapeutic treatment of β-thalassaemia.

Pharmaceutically acceptable salts of the above-described structural analogues of distamycin are salts with pharmaceutically acceptable inorganic or organic acids, such as, for example, hydrochloric acid, hydrobromic acid, sulphuric acid, nitric acid, acetic acid, propionic acid, succinic acid, malonic acid, citric acid, tartaric acid, methanesulphonic acid, p-toluenesulphonic acid.

As has been recently described (9, 10), a combined treatment with various modifiers of the transcription process permits a further increase in the expression of genes for γ-globin.

A second aspect of the present invention is therefore the use of the above-described distamycin analogues or their pharmaceutically acceptable salts in combination with at least one further modifier of the transcription process for the preparation of a medicament for the treatment of β-thalassaemia.

According to a preferred embodiment, the further modifier of the transcription process is selected from the group consisting of cytosine arabinoside, retinoic acid, plicamycin, hydroxyurea, guanine, guanosine triphosphate (GTP), guanosine diphosphate (GDP) and guanosine monophosphate (GMP); of those, cytosine arabinoside and retinoic acid are more preferred.

The activity of the distamycin analogues described previously as inducers of erythroid cell differentiation was evaluated by studying the erythroid differentiation induced in human cell cultures.

The results of the study are illustrated in Table 1 given hereinafter.

The following Example is provided for the purposes of illustration and is not intended to limit the scope of the invention in any way.

EXAMPLE

An evaluation was carried out in respect of the biological activity of five compounds which are referred to herein as "compound 1", "compound 2", "compound 3", "compound 4" and "compound 5" and which belong, respectively, to the series having the general formula (I), (II), (III), (IV) and (V):

Compound 1:

3-(1-methyl-4-(1-methyl-4-(1-methyl-4-(4-(N,N-bis(2-chloroethyl)amino)benzenecarboxamido)pyrrole-2-carboxamido) pyrrole-2-carboxamido)pyrrole-2-carboxamido) propionamidine hydrochloride:

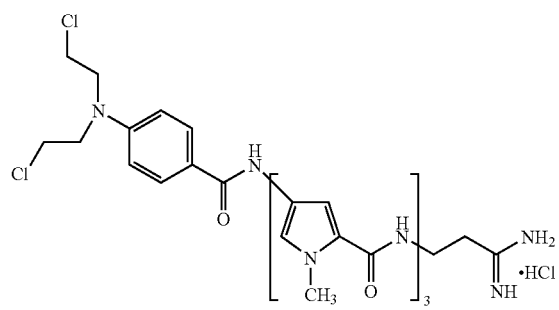

COMPOUND 1

Compound 2:

3-(1-methyl-4-(1-methyl-4-(1-methyl-4-(4-(N,N-bis(2-chloroethyl)amino)benzenecarboxamido)imidazole-2-carboxamido)pyrrole-2-carboxamido)pyrrole-2-carboxamido) propionamidine hydrochloride:

Compound 3:

3-(1-methyl-4-(1-methyl-4-(1-methyl-4-(5-N,N-bis(2-chloroethyl)aminobenzofurane-2-carboxamido)pyrrole-2-carboxamido)pyrrole-2-carboxamido)pyrrole-2-carboxamido)propionamidine hydrochloride:

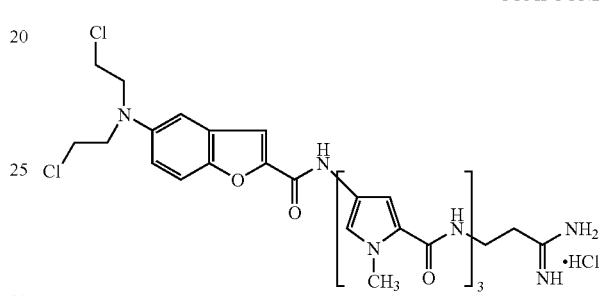

COMPOUND 3

Compound 4:

N-(3'-dimethylaminopropyl)-5-(5-(4-(bis(2-chloroethyl) amino)benzoylamino)-1H-indol-2-carboxamido)benzofurane-2-carboxamido hydrochloride:

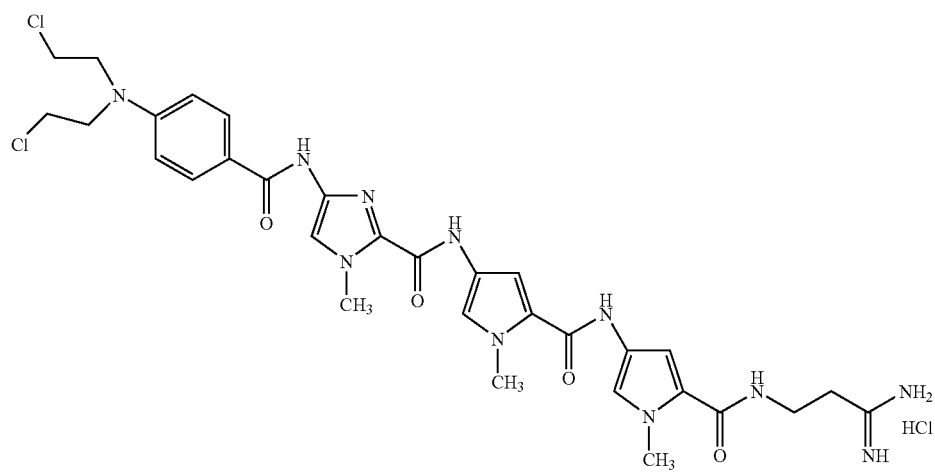

COMPOUND 2

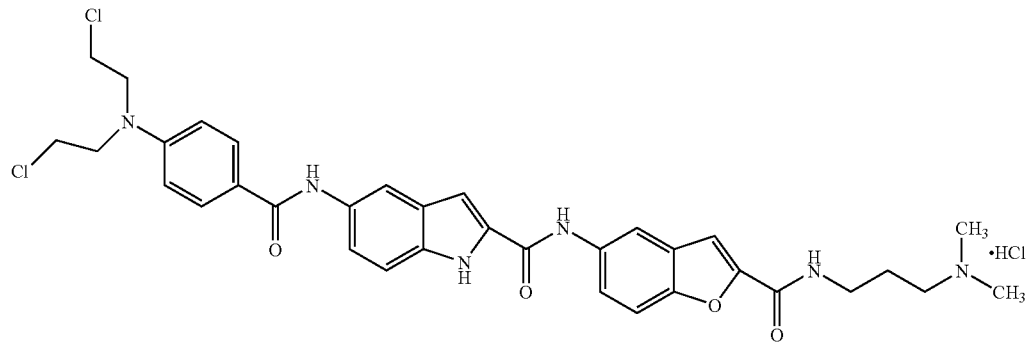

COMPOUND 4

Compound 5:
3-(1-methyl-4-(1-methyl-4-(1-methyl-4-(N,N-bis(2-oxiranylmethyl)amino)pyrrole-2-carboxamido)pyrrole-2-carboxamido)pyrrole-2-carboxamido)cyanopropionamidine hydrochloride:

COMPOUND 5

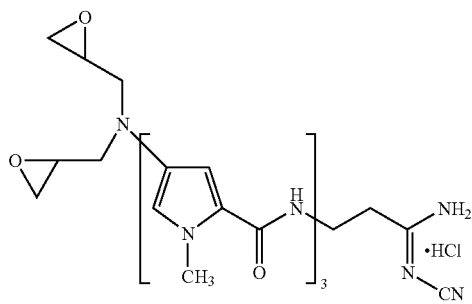

The biological activity was evaluated by examining the capacity of those compounds to induce erythroid differentiation in the human cell line K562, which is capable of undergoing erythroid differentiation by expressing the genes for γ-globin if subjected to treatment with modifiers of the biological response that are suitable for the purpose (19-24). The level of differentiation was evaluated by analysing the positive reaction of the cells to benzidine (23). Some of the data obtained are given in Table 1, which represents the results of five independent experiments (mean±SD). As will be readily appreciated, compounds 1-5 are capable of bringing about an increase in the percentage of K562 cells that react positively to benzidine, compared with untreated control K562 cells.

The production of haemoglobin was evaluated by electrophoresis on cellulose acetate and by colouring the gel with a solution based on benzidine/$H_2O_2$ (23). The chief haemoglobin produced by K562 cells treated with compounds 1-5 is Hb Portland (ζ2γ2)

The expression of genes coding for γ-globins was evaluated by RT-PCR (reverse transcriptase PCR) and Northern blotting (25). The data obtained demonstrate an 8- to 10-fold increase in the intracytoplasmic accumulation of mRNA for γ-globin. The evaluations were carried out after 6 days' induction with the indicated molecules.

An example relating to the results obtained by carrying out a quantitative RT-PCR is shown in Table 2.

In addition, in order to check whether distamycin analogues capable of inducing differentiation of K562 cells were also capable of stimulating the production of HbF in human erythroid precursors isolated from peripheral blood, the technique published by Fibach et al. (26, 27) was used.

The results obtained demonstrated an increased production of HbF in cells treated with distamycin derivatives capable of bringing about an increase in the transcription of genes for γ-globin in K562 cells.

TABLE 1

| Compound | Concentration (nM) | *erythroid differentiation (%) |
|---|---|---|
| — | — | 5.1 ± 3.7 |
| 1 | 50 | 65.5 ± 8.8 |
| 2 | 50 | 85.2 ± 12.8 |
| 3 | 100 | 72.4 ± 10.2 |
| 4 | 500 | 30 ± 3.8 |
| 5 | 50 | 77 ± 10.1 |

*Erythroid differentiation = percentage of K562 cells that react positively to benzidine.

TABLE 2

| Compound | Concentration (nM) | *mRNA for γ-globin |
|---|---|---|
| — | — | 1 |
| 1 | 50 | 11.5 ± 2.5 |

*The accumulation of RNA for γ-globin is given in the Table as an increase compared with that of untreated control K562 cells.

The Technique used is that of quantitative RT-PCR (28, 29) using the following oligonucleotide primers and probe: γ-globin forward primer, 5'-TGG CAA GAA GGT GCT GAC TTC-3'; γ-globin reverse primer, 5'-TCA CTC AGC TGG GCA AAG G-3'; probe γ-globin, 5'-FAM-TGG GAG ATG CCA TAA AGC ACC TGG-TAMRA-3'(FAM=6-carboxy fluorescein, TAMRA=6-carboxy-N,N,N',N'-tetramethylrhodamine).

BIBLIOGRAPHY

1. Al-Khatti A, Papayannopoulou T, Knitter G, Fritsch E F, Stamatoyannopoulos G, Blood, 72:817-819, 1988.
2. DeSimone J, Heller P, Hall L, Zwiers D, Proc. Natl. Acad. Sci. USA, 79:4428-4431, 1982.
3. Lowrey C H, Nienhuis A W, Engl. J. Med., 329:845-848, 1993.
4. Perrine S P, Ginder G D, Faller D V, et al., N. Engl. J. Med., 328:81-86, 1993.

5. Rodgers G P, Dover G J, Uyesaka N, Noguchi C T, Schechter A N, Nienhuis A W, N. Engl. J. Med., 328:73-80, 1993.
6. Rodgers G P, Rachmilewitz E A, British J. Haematology, 91:263-268, 1995.
7. Torkelson S, White B, Faller D V, Phipps K, Pantazis C, Perrine S P, Blood Cells, Molecules and Diseases, 22:150-158, 1996.
8. Rochette J, Craig J E, Thein S L, Blood Reviews, 8:213-224, 1994.
9. Bianchi N, Ongaro F, Chiarabelli C, Gualandi L, Mischiati C, Bergamini P, Gambari R, Biochem. Pharmacol. 60:31-40, 2000.
10. Bianchi N, Osti F, Rutigliano C, Ginanni Corradini F, Borsetti E, Tomassetti M, Mischiati C, Feriotto G, Gambari R, British Journal of Haematology, 104:258-263, 1999.
11. Castaigne S, Chomienne C, Daniel M T, Ballerini P, Berger R, Fenaux P, Degos L., Blood, 76:1704, 1990.
12. Dover G J, Brusilow S, Samid D, New England Journal of Medicine, 327:569-570, 1992.
13. Ikuta T, Atweh G, Boosalis V, White G L, De Fonseca S, Boosalis M, Faller D V, Perrine S P, Annals of New York Academy of Sciences, 850:87-99, 1998.
14. D'Alessio R, Geroni C, Biasoli G, Pesenti E, Grandi M, Mongelli N, Bioorg. & Med. Chem. Lett., 4:1467-1472, 1994.
15. Baraldi P G, Romagnoli R, Spalluto G, Cozzi P, Mongelli N, Bianchi N, Gambari R, Arzneimittel-Forschung/Drug Research, 50: 309-315, 2000.
16. Cozzi P, Baraldi P G, Beria I, Caldarelli M, Capolongo L, Romagnoli R, Spalluto G, WO 98/21202 (1998).
17. Wang W, Lown J W, J. Med. Chem., 35:2890-2897, 1992.
18. Beria I, Pesenti E, Capolongo L, Mongelli N, Baraldi P G Pharmacia S.P.A, WO96/05196 (1996).
19. Animati F, Arcamone F, Lombardi P, Rossi C A, Menarini & Myers Squibb WO 94/25436 (1994)
20. osti F, Corradini F G, Hanau S, Matteuzzi M, Gambari R, Haematologica. 82:395-401, 1997.
21. Lozzio C B, Lozzio B B, Blood, 45:321-334, 1975.
22. Gambari R, Amelotti F, Piva R., Experientia, 41:673-675, 1985.
23. Gambari R, del Senno L, Barbieri R, Cell Differentiation, 14:87-97, 1984.
24. Rutherford T R, Clegg J B, Weatherall D J, Nature, 280: 164-165, 1979.
25. Sambrook J, Fritsch, E F, Maniatis T, Extraction, purification and analysis of messenger RNA from eukaryotic cells. In: Molecular Cloning 2nd ed. Cold Spring Harbor, N.Y., Cold Spring Harbor Laboratory, 7.43-7.45, 1981.
26. Fibach E, Hemoglobin, 22: 45-458, 1998.
27. Fibach E, Burke K P, Schechter A N, Noguchi C T, Rodgers G P, Blood, 81:1630-1635, 1993.
28. Heid C A, Stevens J, Livak K J, Williams P M, Genome Research, 6:986-994, 1996.
29. Gibson U E, Heid C A, Williams P M, Genome Research, 6:995-1001, 1996.

The invention claimed is:
1. A method of treating β-thalassemia, comprising:
administering as a medicament, to a patient suffering from β-thalassemia, a structural analogue of distamycin selected from the group consisting of:

compounds of formula (I):

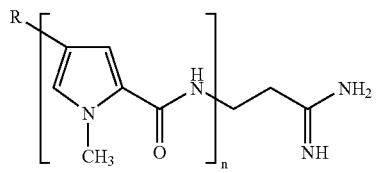

in which:
n is an integer selected from 2, 3 and 4,
R is 4-[(ZCH$_2$CH$_2$)$_2$N]C$_6$H$_4$CONH, and
Z is selected from the group consisting of F, Cl, Br and I;
compounds of formula (II):

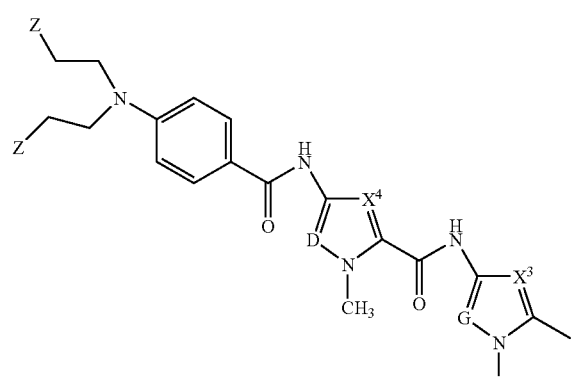

in which:
n is an integer selected from 0 (zero), 1 and 2,
Z is selected from the group consisting of F, Cl, Br and I,
A, B, C and D are each CH,
X$^1$, X$^2$, X$^3$ and X$^4$ are each CH;
compounds of formula (III):

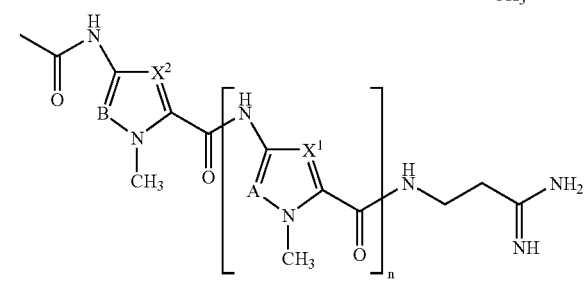

in which:
n is an integer selected from 2, 3 and 4,
T is selected from the group consisting of 4-[(ZCH$_2$CH$_2$)$_2$ N]C$_6$H$_4$CONH,(ZCH$_2$CH$_2$)$_2$N, and CH₂=CZCONH,
Z is selected from the group consisting of Cl, Br, F and I,
E is selected from the group consisting of O (oxygen), S and NR₁,
R₁ is H or CH₃, and
G is CH or N;
compounds of formula (IV):

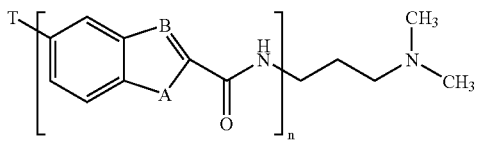

in which:
n is an integer selected from 1, 2, 3 and 4;
T is selected from the group consisting of 4-[(ZCH₂CH₂)₂N]C₆H₄CONH, (ZCH₂CH₂)₂N, and CH₂=CZCONH;
Z is selected from the group consisting of F, Cl, Br and I;
A is selected from the group consisting of O (oxygen), S and NR₁;
R₁ is linear or branched alkyl having from 1 to 4 carbon atoms;
B is CH or N;
compounds of formula (V):

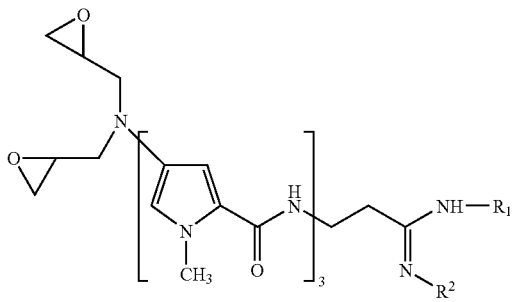

in which:
R₁ and R₂ are selected independently of one another from the group consisting of hydrogen, linear or branched alkyl having from 1 to 4 carbon atoms, nitrile (CN) and hydroxyl (OH), or R₁ and R₂ form, in combination with one another, a linear alkyl chain —(CH₂)m — in which m is 2 or 3;
and their pharmaceutically acceptable salts.

2. The method of claim 1, wherein the structural analogue or its pharmaceutically acceptable salt is in combination with at least one other modifier of the transcription process selected from the group consisting of cytosine arabinoside, retinoic acid, plicamycin, mithramycin, hydroxyurea, guanine, guanosine triphosphate (GTP), guanosine diphosphate (GDP) and guanosine monophosphate (GMP).

3. The method of claim 1, wherein the structural analogue is 3-(1-methyl-4-(1-methyl-4-(1-methyl-4-(4-(N,N-bis(2-chloroethyl)amino)benzenecarboxamido)pyrrole-2-carboxamido)pyrrole-2-carboxamido)pyrrole-2-carboxamido) propionamidine or a pharmaceutically acceptable salt thereof.

4. The method of claim 1, wherein the structural analogue is 3-(1-methyl-4-(1-methyl-4-(1-methyl-4-(4-(N,N- bis(2-chloroethyl)amino)benzenecarboxamido)imidazole-2-carboxamido)pyrrole-2-carboxamido)pyrrole-2-carboxamido) propionamidine or a pharmaceutically acceptable salt thereof.

5. The method of claim 1, wherein the structural analogue is 3-(1-methyl-4-(1-methyl-4-(1-methyl-4-(5-N,N-bis(2-chloroethyl)aminobenzofurane-2-carboxamido)pyrrole-2-carboxamido)pyrrole-2-carboxamido)pyrrole-2-carboxamido) propionamidine or a pharmaceutically acceptable salt thereof.

6. The method of claim 1, wherein the structural analogue is N(3'-dimethylaminopropyl)-5-(5-(4-(bis(2-chloroethyl)amino)benzoylamino)-1H-indol-2-carboxamido)-benzofurane-2-carboxamido or a pharmaceutically acceptable salt thereof.

7. The method of claim 1, wherein the structural analogue is 3-(1-methyl-4-(1-methyl-4-(1-methyl-4-(N,N-bis(2-oxiranylmethyl)amino)pyrrole-2-carboxamido)pyrrole-2-carboxamido)pyrrole-2-carboxamido)cyanopropionamidine or a pharmaceutically acceptable salt thereof.

8. The method of claim 1, wherein the pharmaceutically acceptable salt is a salt of an acid selected from the group consisting of hydrochloric acid, hydrobromic acid, sulphuric acid, nitric acid, acetic acid, propionic acid, succinic acid, malonic acid, citric acid, tartaric acid, methanesulphonic acid and p-toluenesulphonic acid.

9. The method of claim 2, wherein the structural analogue is 3-(1-methyl -4-(1-methyl-4-(1-methyl-4-(4-(N,N-bis(2-chloroethyl)amino)benzenecarboxamido)pyrrole-2-carboxamido)pyrrole-2-carboxamido)pyrrole-2-carboxamido) propionamidine or a pharmaceutically acceptable salt thereof.

10. The method of claim 2, wherein the structural analogue is 3-(1-methyl-4-(1-methyl-4-(1-methyl-4-(4-(N,N-bis(2-chloroethyl)amino)benzenecarboxamido)imidazole-2-carboxamido)pyrrole-2-carboxamido)pyrrole-2-carboxamido) propionamidine or a pharmaceutically acceptable salt thereof.

11. The method of claim 2, wherein the structural analogue is 3-(1-methyl-4-(1-methyl-4-(1-methyl-4-(5-N,N-bis(2-chloroethyl)aminobenzofurane-2-carboxamido)pyrrole-2-carboxamido)pyrrole-2-carboxamido)pyrrole-2-carboxamido) propionamidine or a pharmaceutically acceptable salt thereof.

12. The method of claim 2, wherein the structural analogue is N(3'-dimethylaminopropyl)-5-(5-(4-(bis(2-chloroethyl)amino)benzoylamino)-1H-indol-2-carboxamido)-benzofurane-2-carboxamido or a pharmaceutically acceptable salt thereof.

13. The method of claim 2, wherein the structural analogue is 3-(1-methyl-4-(1-methyl-4-(1-methyl-4-(N,N-bis(2-oxiranylmethyl)amino)pyrrole-2-carboxamido)pyrrole-2-carboxamido)pyrrole-2-carboxamido)cyanopropionamidine or a pharmaceutically acceptable salt thereof.

14. The method of claim 2, wherein the pharmaceutically acceptable salt is a salt of an acid selected from the group consisting of hydrochloric acid, hydrobromic acid, sulphuric acid, nitric acid, acetic acid, propionic acid, succinic acid, malonic acid, citric acid, tartaric acid, methanesulphonic acid and p-toluenesulphonic acid.

* * * * *